(12) United States Patent
Clark

(10) Patent No.: US 6,717,707 B2
(45) Date of Patent: Apr. 6, 2004

(54) METHOD AND SYSTEM FOR CONTROLLING RESONANCE WITHIN A RESONATOR-ENHANCED OPTICAL SYSTEM

(75) Inventor: Bryan Clark, Mountain View, CA (US)

(73) Assignee: Beyond 3, Inc., Fremont, CA (US)

( * ) Notice: Subject to any disclaimer, the term of this patent is extended or adjusted under 35 U.S.C. 154(b) by 0 days.

(21) Appl. No.: 10/329,741

(22) Filed: Dec. 23, 2002

(65) Prior Publication Data

US 2003/0128435 A1 Jul. 10, 2003

Related U.S. Application Data

(63) Continuation-in-part of application No. 10/002,425, filed on Oct. 23, 2001, and a continuation-in-part of application No. 09/933,225, filed on Aug. 20, 2001, and a continuation-in-part of application No. 09/871,512, filed on May 30, 2001, and a continuation-in-part of application No. 09/789,913, filed on Feb. 21, 2001, now Pat. No. 6,522,471.

(51) Int. Cl.[7] .............................. G02F 1/00; G02F 1/03; G01N 21/00; G01B 9/02
(52) U.S. Cl. ....................... 359/237; 359/245; 359/260; 356/237.2; 356/237.3; 356/237.4; 356/519; 250/201.3; 372/24
(58) Field of Search ................................ 359/237, 245, 359/247, 260, 629, 248; 356/237.1, 237.2, 237.3, 237.4, 345, 454, 450, 519; 250/201.3, 358.1; 372/20, 24, 26; 385/10, 14, 16, 24

(56) References Cited

U.S. PATENT DOCUMENTS

| | | | |
|---|---|---|---|
| 3,901,597 A | | 8/1975 | White |
| 4,659,224 A | | 4/1987 | Monchalin |
| 5,220,403 A | | 6/1993 | Batchelder et al. |
| 5,345,328 A | * | 9/1994 | Fritz et al. .................. 359/248 |
| 6,407,373 B1 | * | 6/2002 | Dotan ...................... 250/201.3 |
| 6,449,037 B2 | * | 9/2002 | Jun et al. .................. 356/237.4 |
| 6,594,022 B1 | * | 7/2003 | Watterson et al. .......... 356/519 |
| 6,597,448 B1 | * | 7/2003 | Nishiyama et al. ....... 356/237.4 |
| 6,606,153 B2 | * | 8/2003 | Marxer et al. ............ 356/237.3 |
| 6,611,325 B1 | * | 8/2003 | Clark ...................... 356/237.2 |

* cited by examiner

Primary Examiner—Loha Ben
(74) Attorney, Agent, or Firm—Jeffrey D. Moy; A. Mitchell Harris; Weis, Moy & Harris, P.C.

(57) ABSTRACT

A method and system for controlling resonance within a resonator-enhanced optical system provides improved tracking performance in resonator-enhanced optical measurement and data storage and retrieval systems. The system includes an illumination subsystem and a detection subsystem with an optical resonator interposed in an optical path between the illumination subsystem and the detection subsystem. The resonance of the optical resonator is tuned, either by changing the wavelength of the illumination subsystem or the geometric path length within the resonator. Closed-loop feedback control signals can thereby maintain resonance at a desired operating point. The feedback control signal components can be further used to provide measurement data if the resonance of the optical resonator is a function of a measured surface, such as when a reflective surface of the resonator is a surface under measurement.

22 Claims, 5 Drawing Sheets

METHOD AND SYSTEM FOR CONTROLLING RESONANCE WITHIN A RESONATOR-ENHANCED OPTICAL SYSTEM

RELATED APPLICATIONS

This application is a continuation-in part of U.S. Patent Application "SYSTEM OF BEAM NARROWING FOR RESOLUTION ENHANCEMENT AND METHOD THEREFOR", Ser. No. 09/789,913 filed on Feb. 21$^{st}$, 2001 and is further now U.S. Pat No. 6,522,071 a continuation-in-part of pending U.S. Patent Applications from which it claims the benefit of priority under 35 U.S.C. §120: OPTICAL STORAGE METHOD AND APPARATUS HAVING ENHANCED RESOLUTION", Ser. No. 09/871,512, filed May 30$^{th}$, 2001; "OPTICAL MEASUREMENT AND INSPECTION METHOD AND APPARATUS HAVING ENHANCED OPTICAL PATH DIFFERENCE DETECTION", Ser. No. 09/933,225, filed Aug. 20$^{th}$, 2001; and "OPTICAL INSPECTION METHOD AND APPARATUS HAVING AN ENHANCED HEIGHT SENSITIVITY REGION AND ROUGHNESS FILTERING" Ser. No. 10/002,425, filed Oct. 23$^{rd}$, 2001. The specifications all of the above-listed applications are incorporated herein by reference.

BACKGROUND OF THE INVENTION

1. Field of the Invention

This invention relates to optical systems, and more specifically, to optical systems that incorporate an optical resonator in either the illumination path or a measurement path in order to enhance the optical performance of the system.

2. Description of the Related Art

Optical measurement systems, optical storage and retrieval systems and other optical systems may be limited by many factors, including illumination beam size, diffraction limit, detector noise, and resolution. The above-incorporated patent applications disclose techniques for enhancing the performance of a variety of optical systems and improving the resolution and sensitivity of optical technologies disclosed therein.

It would be further desirable to improve the performance of the systems disclosed in the above-referenced patent applications, as well as other optical systems, in order to further improve their performance.

SUMMARY OF THE INVENTION

The foregoing objectives are achieved in an optical system and method and apparatus having improved optical performance. The system includes an optical illumination subsystem, an optical detection subsystem and an optical resonator disposed in at least one optical path between the illumination system and the detection system. The system further includes a tuning stage that may be incorporated within the resonator or the illumination subsystem to provide adjustment of the resonance of the optical resonator either by adjusting the wavelength of light passing through the resonator or by adjusting an optical path length within the resonator in order to assure the proper resonance operating point.

Control signals used in a closed-loop system for controlling the resonator may also be used for output of measured data. In particular, components of the resonance control signal provide information about the changing resonant path length of the resonator, which may be a measurement function of the system.

The foregoing and other objects, features, and advantages of the invention will be apparent from the following, more particular, description of the preferred embodiment of the invention, as illustrated in the accompanying drawings.

DESCRIPTION OF EMBODIMENTS OF THE INVENTION

The above-referenced patent applications describe various resonator-enhanced optical systems, such as optical storage data and retrieval systems having improved data density, illumination sources having narrowed beam widths and optical measurement systems having improved resolution and contrast and having improved detector phase/amplitude slope characteristics controlled over portions of the detector response. The above-recited improvements are developed by placement and tuning of resonators within the optical paths of the associated systems, in order to optimize the operating point on the resonator response function.

Figure 1:
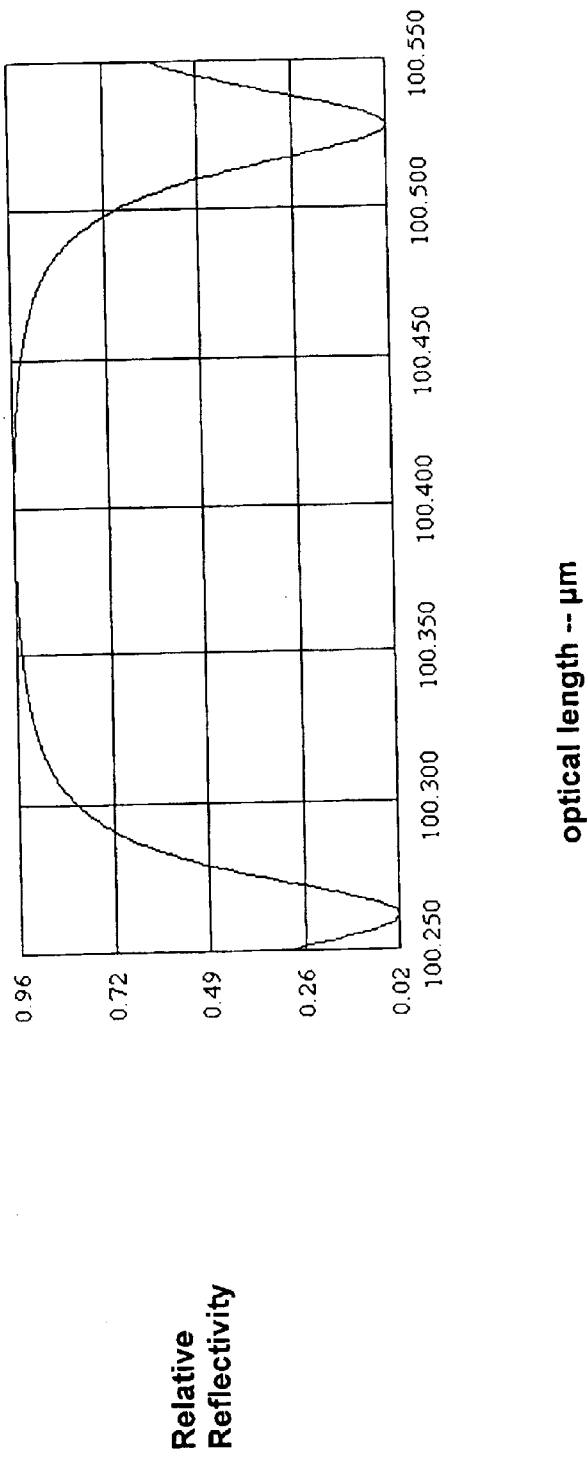
FIG. 1 is a graph depicting the response of an optical resonator that may be included in an optical system in accordance with an embodiment of the present invention.

While the incorporation of a resonator improves the performance of the systems described within the above-incorporated patent applications, the resonator must be tuned precisely to a specific point in the response function. With reference to FIG. 1, it is observed that the response curve of an optical resonator is very sharp near the resonances and almost flat for operating points between them, which corresponds to the physical basis for resonator sensitivity. Therefore, it is mandatory that the resonator be tuned so that the functioning point lies in the correct position on the response curve. Moreover, the above-described position corresponding to resonator optical length does not have to be accurate. The operating position (and corresponding operating point) may be set to any of the resonating positions, which occur at half-wavelength intervals, but the selected operating point must be very stable. Even nanometric changes will significantly affect the sensitivity of the device. The above-described requirements are made even more stringent when the resonator operating point is set slightly off of resonance, producing improved phase slope contrast for use in particular applications of embodiments of the present invention.

Precise control of the resonator mechanical structure and illumination frequency (wavelength) is therefore required in resonator-enhanced systems and in many of the disclosed systems. When dynamic tuning of the resonance operating point must be provided within an optical system, an electro-mechanical positioner is included to provide the tuning capability. However, the agility of a mechanical positioning system places a limitation on the rate and depth of variations that can either be accepted or rejected by the optical system, depending on how the optical system is being used. For example, in a resonator-enhanced optical surface inspection system, the size of larger surface variations (surface slope) determines the magnitude of the mechanical compensation that must be applied to a movable partially reflective surface forming part of the resonator, and therefore the agility (response) of the mechanical positioning subsystem determines the maximum rate of scanning in order for the system to stay within a predetermined resonance operating point window.

The present invention includes a tuning subsystem that generally employs electronic/electrical means for maintaining the predetermined resonance operating point of the systems disclosed in the above-incorporated patent applications as well as any other resonance-enhanced optical system. Mechanical means may alternatively be employed. A feedback control system is employed to maintain the resonator frequency at a predetermined operating point in conformity with detected variations in the received optical signal. The detection information can be filtered and used to provide either data extraction (for optical storage and retrieval systems) or measurement information (for inspection and measurement systems).

Figure 2:
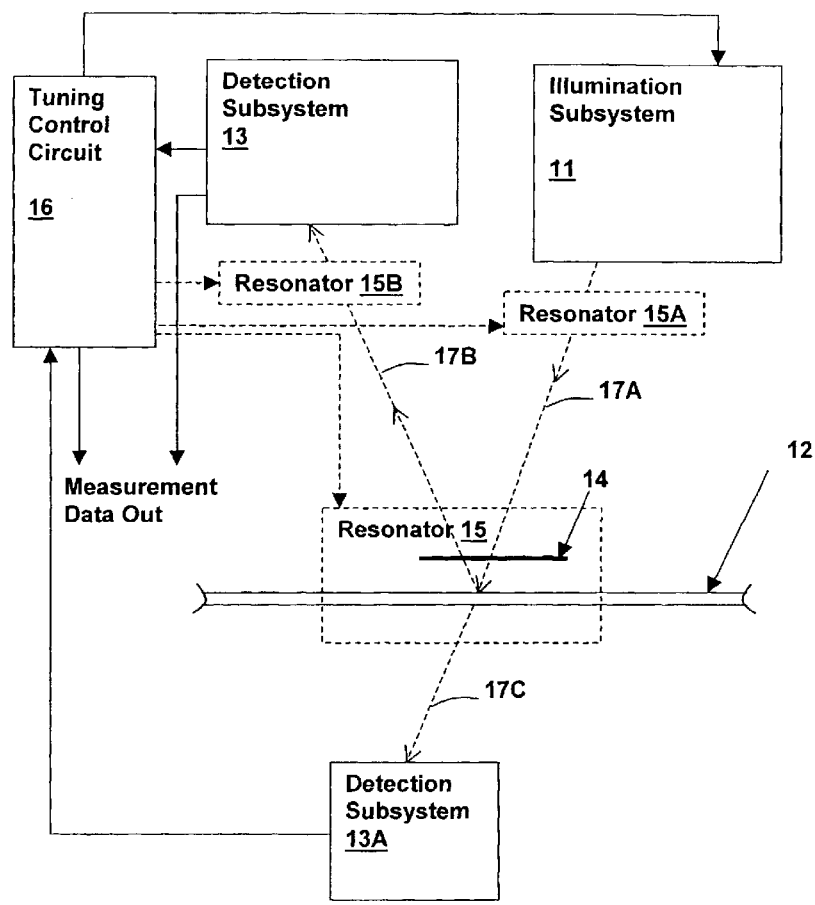
FIG. 2 is an illustration depicting an optical system in accordance with an embodiment of the present invention.

With reference now to the figures, and particularly to FIG. 2, a surface or volume 12 including features under detection or data that is being extracted is illuminated by an illumination beam 17A. A reflected beam 17B and/or a transmitted beam 17C is detected by a detection subsystem 13 and/or 13A, providing measurement information or data extraction. At least one resonator 15, 15A and/or 15B is positioned within the optical path of the illumination beam 17A, reflected beam 17B and/or transmitted beam 17C and is tuned at a predetermined operating point to provide the desired characteristics at detection subsystem 13 and/or 13A.

For example, in beam narrowing applications, resonator 15A is employed to reduce the profile of illumination beam 17A. Resonator 15A may be included within illumination subsystem 11 or located between illumination subsystem and surface 12 as shown. Alternatively, or in combination, resonator 15 may be employed at surface 12 to increase sensitivity of the optical system. Resonator 15 includes a partially reflective surface 14 positioned above surface 12 at a predetermined distance to provide a predetermined resonance operating point. The predetermined resonator optical length may be maintained with control signals from tuning control circuit 16 acting mechanically (in general piezo-movement) on the partially reflective surface 14, by introducing an optical retarder in the illumination beam (e.g. an electro-optical liquid or crystal), or by controlling the frequency (wavelength) of illumination subsystem 11. Without limitation with respect to the specific manner of optical resonance control provided, the control is performed in response to signals from tuning control circuit 16. Either mechanism or a combination may be used to maintain the resonance operating point of resonator 15, 15A and/or 15B.

Detection subsystem 13 provides information to tuning control circuit 16 so that deviations from the resonance operating point can be detected, which is generally a deviation from an intensity level (which may be "dark" or "gray" level) of an interferometric fringe detection (e.g., a dark level detector located at one of the fringe lines formed inside the resonator and detected in one of beams 17B or 17C). Measurement data or data extraction may be produced by detection subsystem 13 and/or 13A or by extracting components of the feedback control signals from tuning control circuit 16 or both sources of information may be processed and used.

Figure 3A:
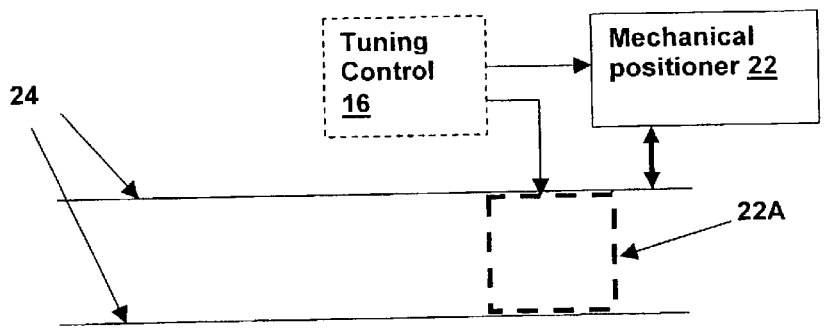
FIGS. 3A and 3B are pictorial diagrams depicting exemplary resonator tuning elements that may be incorporated within the optical system of FIG. 1.

Referring now to FIG. 3A, a first set of mechanical resonator tuning control mechanisms that may be employed within resonators 15, 15A and/or 15B is depicted. Tuning control 16 controls either a mechanical positioner 22 as described in the above-incorporated patent applications, or an alternative mechanical positioner 22A to control the spacing between a pair of partially reflective surfaces 24. One of partially reflective surfaces 24 may be a measured surface such as surface 12 and may be fully reflective or absorptive/reflective if a reflection-only measurement is being made (i.e., there is no transmission measurement). Positioner 22A may be a piezo electric element disposed between the two partially reflective surfaces 24 and an electrical signal supplied by tuning control 16 effectively controls the size of positioner 22A and therefore the spacing between partially reflective surfaces 24. Positioner 22 is a voice-coil, piezoelectric or other positioner that moves the top partially reflective surface in applications where the bottom partially reflective surface is fixed or is a surface under measurement.

Figure 3B:
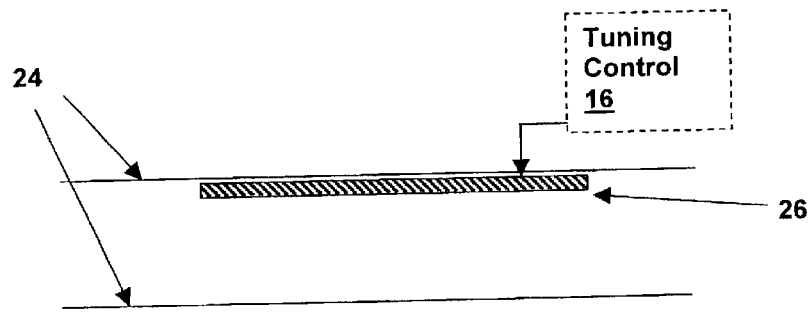

Referring now to FIG. 3B, a second set of electrical/electronic resonator tuning control mechanisms that may be employed within resonators 15, 15A and/or 15B is depicted. Tuning control 16 controls an optical path length within resonators 15, 15A and/or 15B using a segment of refractive material 26 disposed between partially reflective surfaces 24. As described above, one of partially reflective surfaces 24 may be a measured surface such as surface 12 and may be fully reflective or absorptive/reflective if a reflection-only measurement is being made (i.e., there is no transmission measurement).

Refractive material 26 controls the resonance operating point between partially reflective surfaces 24 in response to a signal from tuning control 16, which may apply an electrical potential across refractive material 26 or produce a current through refractive material 26. The electrical signal changes either the refractive index of refractive material 26, or the effective thickness of refractive material 26, either of which will alter the optical path length through refractive material 26, permitting tuning of the optical length of the resonator formed between partially reflective surfaces 24. The refractive index of refractive material 26 may be adjusted by biasing a semiconductor or thin-film material sensitive to an electric field or transverse current, producing a change in refractive index. Alternatively, the effective thickness of refractive material 26 may be adjusted by using an electro-optical crystal or liquid.

The illustrations of FIGS. 2A and 2B show mechanisms for adjusting resonators 15, 15A and/or 15B of FIG. 2 consistent with maintaining a desired resonance operating point, as illustrated in FIG. 1. The selection of a mechanical vs. electrical tuning system is generally a performance-driven process. While the electrical tuning system may be more costly, the tuning agility is higher, yielding a measurement or data storage/retrieval that has a higher measurement speed or data rate. It is alternatively possible to maintain the resonance operating point of the resonator by controlling the illumination frequency of illumination subsystem 11 and using one or more resonators having a fixed mechanical length.

Figure 4A:
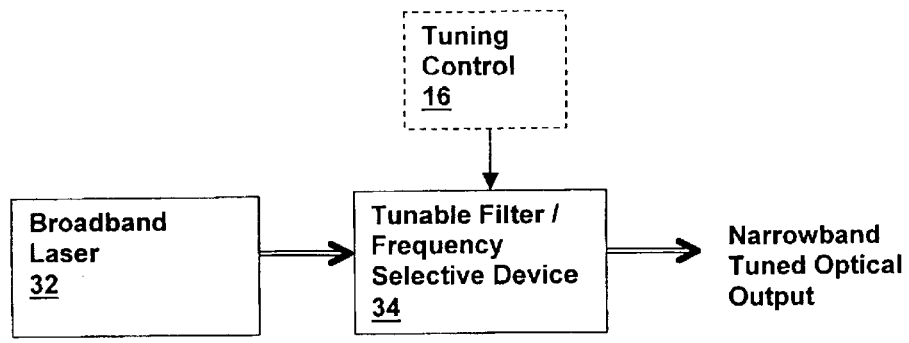
FIGS. 4A and 4B are pictorial diagrams depicting exemplary illumination source tuning elements that may be incorporated within the optical system of FIG. 1.

Referring now to FIG. 4A a first illumination source is depicted that incorporates a broadband laser 32 coupled to a tunable filter or frequency selective device 34 that is controlled by a signal from tuning control 16. Tunable filter 34 selects a narrow portion of the output of broadband laser 32 so that frequency may be varied within a small but usable range. The above-described type of illumination source is known as a tunable external cavity laser (ECL).

Figure 4B:
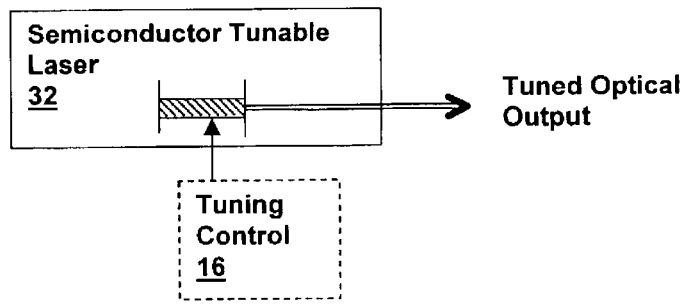

Another suitable illumination source is shown in FIG. 4B. A semiconductor tunable laser 32 is coupled to tuning control 16. Semiconductor tunable laser 32 provides a narrowband output that is directly controllable by a signal from tuning control 16. Suitable lasers are dictated by system requirement as some lasers are more agile, which affects measurement speed or data storage/retrieval rates as described above for resonator control. Suitable types of lasers are Distributed-feedback (DFB) lasers, distributed Bragg reflector (DBR) lasers and vertical cavity surface emitting lasers (VCSEL).

Figure 5:
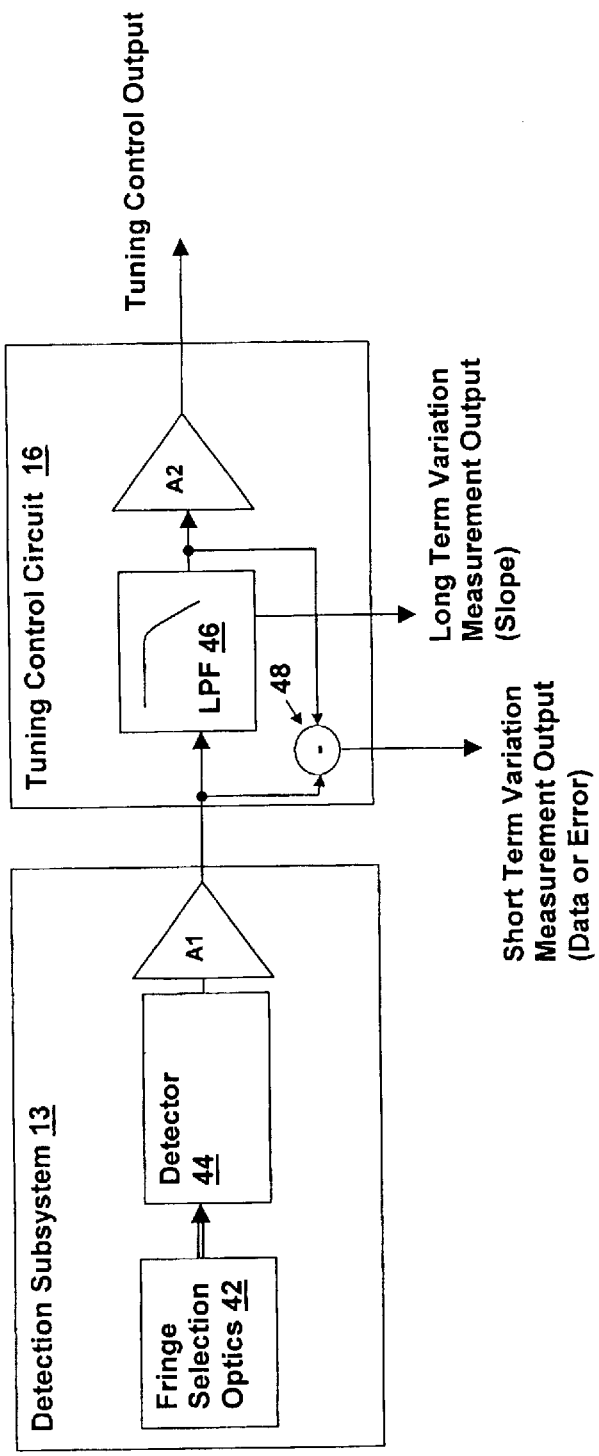
FIG. 5 is a block diagram of a tuning system in accordance with an embodiment of the invention.

Referring now to FIG. 5, details of the detection and control systems in accordance with an embodiment of the present invention are depicted. Detection subsystem 13 includes fringe selection optics 42 that selects the interferometric detection point as the output to detector 44. Amplifier A1 adjusts the gain and offset of detector output 44 to provide a control signal to tuning control circuit 16. Alternatively, amplifier A1 may act as a comparator, comparing the output of detector 44 to a threshold, so that tuning control circuit is alerted that the contrast of the optical system has deviated from ideal due to a shift in the resonance operating point. The two alternative amplifier A1 schemes described above correspond to a continuous vs. discrete feedback control scheme and either alternative is suitable for maintaining the resonance operating point of the optical system.

The output of amplifier A1 enters low pass filter 46 that removes high frequency variations from the detected signal that are due to data (in a data storage/retrieval system) or surface features (in a measurement system). The output of low pass filter 46 is provided to a second amplifier A2 that provides the tuning control output for controlling either the frequency of the illumination source, or the optical length of a resonator. The filtered output of low pass filter 46 may also be provided to measurement circuits as an indicator of long term variation (slope). The output of low-pass filter 46 may be combined with the input of low-pass filter 46 using a difference amplifier 48, yielding a high frequency component output that contains data (in a data storage/retrieval system) or surface feature information (in a measurement system). Alternatively, a separate high-pass filter may be employed to extract the higher frequency components of the detector signal from amplifier A1.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. An optical system comprising:
   an optical illumination subsystem for producing a beam for illuminating a surface;
   an optical detection subsystem for measuring an intensity of light that has left said surface;
   an optical resonator formed by a partially reflective surface and said surface, said partially reflective surface positioned in an optical path between said surface and said optical detection subsystem, whereby a sensitivity of said detection subsystem is enhanced over a range of intensity of said light that has left said surface by maintaining a particular resonant operating point within said optical resonator;
   a scanning subsystem for moving said partially reflective surface with respect to said surface in a plane substantially parallel to said surface; and
   a tuning system for maintaining said particular resonant operating point.

2. The optical system of claim 1, wherein said tuning system comprises:
   a feedback circuit for producing a signal in response to an operating point of said optical resonator deviating said particular resonant operating point; and
   a control mechanism responsive to an output of said feedback circuit for restoring said operating point of said optical resonator.

3. The optical system of claim 2, wherein said control mechanism is contained within said illumination subsystem and adjusts an output frequency of said illumination subsystem.

4. The optical system of claim 3, wherein an illumination source within said illumination subsystem is a tunable laser diode, and wherein said control mechanism is a tuning input of tunable laser diode.

5. The optical system of claim 4, wherein said tunable laser diode is a distributed Bragg reflector (DBR) laser diode, and wherein said tuning input is coupled to said Bragg reflector for adjusting said output frequency of said illumination subsystem.

6. The optical system of claim 4, wherein said tunable laser diode is a distributed feedback (DFB) laser diode, and wherein said tuning input is coupled to a drive current input of said laser diode for adjusting said output frequency of said illumination subsystem.

7. The optical system of claim 4, wherein said tunable laser diode is a vertical cavity surface emitting (VCSEL) laser diode, and wherein said tuning input is coupled to a drive current input of said laser diode for adjusting said output frequency of said illumination subsystem.

8. The optical system of claim 4, wherein said tunable laser diode comprises:
   a broadband laser diode emitting optical radiation having a predetermined greater bandwidth than an output bandwidth of said illumination subsystem; and
   a frequency selective element for selecting a portion of said predetermined greater bandwidth and supplying said portion of said bandwidth to said output of said illumination subsystem.

9. The optical system of claim 8, wherein said tunable laser diode is an external cavity (ECL) laser diode.

10. The optical system of claim 3, wherein said control mechanism is a filter that selects a narrowband portion of a broadband optical output, and wherein a center frequency of said filter is responsive to said output of said feedback circuit.

11. The optical system of claim 2, wherein said control mechanism is a refractive element having a tunable refractive index disposed within said optical resonator, wherein said refractive index is responsive to said feedback signal, whereby said particular resonant operating point may be restored by adjusting said refractive index.

12. The optical system of claim 2, wherein said control mechanism is a refractive element having an electrically adjustable thickness disposed within said optical resonator, wherein said thickness is responsive to said feedback signal, whereby said particular resonant operating point may be restored by adjusting said thickness.

13. The optical system of claim 2, wherein said control mechanism is an electro-optical retarder disposed within said optical resonator, whereby said particular resonant operating point is restored by adjusting a voltage imposed on said electro-optical retarder.

14. The optical system of claim 13, wherein said electro-optical retarder is a liquid crystal.

15. An optical system comprising:

an optical illumination subsystem for producing a beam for illuminating a surface;

an optical detection subsystem for measuring an intensity of light that has left said surface;

tunable resonance means for increasing an optical performance of said optical system over a range of said intensity by forming a resonator with an area of said surface; and scanning means for moving a portion of said tunable resonance means over said surface, whereby said resonance means forms a resonator with a selectable area of said surface.

16. A method for operating an optical system, said method comprising:

illuminating a surface with an illumination beam from an illumination subsystem;

detecting light leaving said surface with a detection subsystem;

enhancing performance of said detecting over a range of said detecting, by providing a partially reflective surface forming a resonance between said surface and said detection subsystem; and maintaining said resonance at a predetermined operating point.

17. The method of claim 16, wherein said maintaining is performed by adjusting a frequency of said illumination subsystem.

18. The method of claim 17, wherein said adjusting is performed by adjusting a filter interposed between an illumination source within said illumination subsystem and an optical output of said illumination subsystem.

19. The method of claim 16, and wherein said maintaining is performed by adjusting an optical path length between said partially reflective surface and said surface.

20. The method of claim 16, further comprising:

generating a control signal for tuning said optical system to maintain said resonance at said predetermined operating point; and measuring said control signal to provide an operational result of said optical system.

21. The method of claim 20, further comprising filtering low frequency components of said control signal to produce a low frequency variant output, and wherein said measuring measures said low frequency variant output.

22. The method of claim 20, further comprising filtering high frequency components of said control signal to produce a high frequency variant output, and wherein said measuring measures said high frequency variant output.

* * * * *